United States Patent
Stobbe et al.

(10) Patent No.: US 11,752,494 B2
(45) Date of Patent: Sep. 12, 2023

(54) CATALYST FOR ALKANE OXIDATIVE DEHYDROGENATION AND/OR ALKENE OXIDATION

(71) Applicant: SHELL OIL COMPANY, Houston, TX (US)

(72) Inventors: Erwin Roderick Stobbe, Amsterdam (NL); Hendrik Albertus Colijn, Amsterdam (NL); Maria Elisabeth Van Es-Hogenstijn, Amsterdam (NL); Johanna Jacoba Berg-Slot, Amsterdam (NL)

(73) Assignee: SHELL USA, INC., Houston, TX (US)

( * ) Notice: Subject to any disclaimer, the term of this patent is extended or adjusted under 35 U.S.C. 154(b) by 0 days.

(21) Appl. No.: 17/284,967

(22) PCT Filed: Oct. 15, 2019

(86) PCT No.: PCT/EP2019/077922
§ 371 (c)(1),
(2) Date: Apr. 13, 2021

(87) PCT Pub. No.: WO2020/078980
PCT Pub. Date: Apr. 23, 2020

(65) Prior Publication Data
US 2021/0354116 A1    Nov. 18, 2021

(30) Foreign Application Priority Data

Oct. 18, 2018  (EP) .................................... 18201198

(51) Int. Cl.
| | |
|---|---|
| B01J 27/057 | (2006.01) |
| B01J 23/00 | (2006.01) |
| B01J 37/04 | (2006.01) |
| B01J 37/08 | (2006.01) |
| C07C 5/48 | (2006.01) |

(52) U.S. Cl.
CPC ......... B01J 27/0576 (2013.01); B01J 23/002 (2013.01); B01J 37/04 (2013.01); B01J 37/082 (2013.01); C07C 5/48 (2013.01); C07C 2523/28 (2013.01)

(58) Field of Classification Search
CPC ...... B01J 27/0576; B01J 23/002; B01J 37/04; B01J 37/082; B01J 2523/00; B01J 37/08; B01J 23/28; C07C 5/48; C07C 2523/28; C07C 2523/16; C07C 5/3332; Y02P 20/52

See application file for complete search history.

(56) References Cited

U.S. PATENT DOCUMENTS

| | | | | |
|---|---|---|---|---|
| 5,637,546 A | * | 6/1997 | Tenten ..................... | B01J 37/08 502/311 |
| 5,973,186 A | * | 10/1999 | Midorikawa .......... | B01J 8/1827 558/319 |
| 7,091,377 B2 | | 8/2006 | Borgmeier et al. | |
| 2004/0147393 A1 | | 7/2004 | Hibst et al. | |
| 2004/0245681 A1 | * | 12/2004 | Dieterle ............... | B01J 37/0223 266/171 |
| 2006/0235238 A1 | * | 10/2006 | Komada ................ | B01J 23/002 502/312 |
| 2007/0203022 A1 | * | 8/2007 | Schlogl .................. | B01J 23/002 502/321 |
| 2008/0248947 A1 | * | 10/2008 | Zajac ...................... | B01J 23/28 558/321 |
| 2010/0256432 A1 | | 10/2010 | Arnold et al. | |
| 2011/0237820 A1 | * | 9/2011 | Besecker ............. | B01J 23/8878 558/324 |
| 2015/0273445 A1 | * | 10/2015 | Bogan, Jr. ............ | B01J 37/0045 502/215 |
| 2019/0232270 A1 | * | 8/2019 | Tateno ................... | B01J 37/088 |

FOREIGN PATENT DOCUMENTS

| | | |
|---|---|---|
| DE | 10360057 A1 | 7/2004 |
| WO | 2003064035 A1 | 8/2003 |
| WO | 2010096909 A1 | 9/2010 |
| WO | 2013164418 A1 | 11/2013 |
| WO | 2014051955 A1 | 4/2014 |

OTHER PUBLICATIONS

International Search Report and Written Opinion Received for PCT Application No. PCT/EP2019/077922, dated Dec. 19, 2019, 10 pages.

* cited by examiner

*Primary Examiner* — Ali Z Fadhel
(74) *Attorney, Agent, or Firm* — SHELL USA, INC.

(57) ABSTRACT

The invention relates to a process for preparing a catalyst for alkane oxidative dehydrogenation and/or alkene oxidation, which catalyst is a mixed metal oxide catalyst containing molybdenum, vanadium, niobium and optionally tellurium, wherein the process comprises: a) preparing a catalyst precursor containing molybdenum, vanadium, niobium and optionally tellurium; b) optionally contacting the catalyst precursor obtained in step a) with oxygen and/or an inert gas at an elevated temperature; c) contacting the catalyst precursor obtained in step a) or step b) with a gas mixture comprising ammonia and water, which gas mixture further comprises oxygen and/or an inert gas, at an elevated temperature; and d) optionally contacting the catalyst precursor obtained in step c) with an inert gas at an elevated temperature. Further, the invention relates to a catalyst obtainable by said process and to a process of the oxidative dehydrogenation of an alkane containing 2 to 6 carbon atoms and/or the oxidation of an alkene containing 2 to 6 carbon atoms wherein said catalyst is used.

9 Claims, No Drawings

CATALYST FOR ALKANE OXIDATIVE DEHYDROGENATION AND/OR ALKENE OXIDATION

CROSS REFERENCE TO RELATED APPLICATIONS

This is a national stage application of International Application No. PCT/EP2019/077922, filed 15 Oct. 2019, which claims benefit of priority to International Patent Application No. 18201198.1, filed 18 Oct. 2018.

FIELD OF THE INVENTION

The present invention relates to a process for preparing a catalyst for alkane oxidative dehydrogenation (oxydehydrogenation; ODH) and/or alkene oxidation, to the catalyst obtainable by such process, and to an alkane ODH and/or alkene oxidation process using such catalyst.

BACKGROUND OF THE INVENTION

It is known to oxidatively dehydrogenate alkanes, such as alkanes containing 2 to 6 carbon atoms, for example ethane or propane resulting in ethylene and propylene, respectively, in an oxidative dehydrogenation (oxydehydrogenation; ODH) process. Examples of alkane ODH processes, including catalysts and other process conditions, are for example disclosed in U.S. Pat. No. 7,091,377, WO2003064035, US20040147393, WO2010096909 and US20100256432. Mixed metal oxide catalysts containing molybdenum (Mo), vanadium (V), niobium (Nb) and optionally tellurium (Te) as the metals, can be used as such oxydehydrogenation catalysts. Such catalysts may also be used in the direct oxidation of alkenes to carboxylic acids, such as in the oxidation of alkenes containing 2 to 6 carbon atoms, for example ethylene or propylene resulting in acetic acid and acrylic acid, respectively.

Further, WO2013164418 discloses a process for preparing a catalyst for alkane oxidative dehydrogenation and/or alkene oxidation, which catalyst is a mixed metal oxide catalyst containing molybdenum, vanadium and niobium, wherein the process comprises: a) preparing a catalyst containing molybdenum, vanadium and niobium; b) contacting the catalyst with oxygen at an elevated temperature, to obtain a mixed metal oxide catalyst containing molybdenum, vanadium and niobium; and c) contacting the catalyst with a gas mixture comprising an inert gas and oxygen, wherein the amount of oxygen is of from 10 to less than 10,000 parts per million by volume (ppmv), based on the total volume of the gas mixture, at an elevated temperature. In the Examples of said WO2013164418, said step b) comprised calcination in static air at 275° C. and said step c) comprised calcination in a nitrogen stream at 600° C. which stream additionally contained a varying amount of oxygen.

It is an object of the present invention to provide a mixed metal oxide catalyst containing Mo, V, Nb and optionally Te which has a relatively high activity and/or a relatively high selectivity in the oxidative dehydrogenation of alkanes containing 2 to 6 carbon atoms, for example ethane or propane, and/or in the oxidation of alkenes containing 2 to 6 carbon atoms, for example ethylene or propylene.

SUMMARY OF THE INVENTION

Surprisingly it was found that a mixed metal oxide catalyst containing Mo, V, Nb and optionally Te having a relatively high activity and/or a relatively high selectivity in the above-mentioned oxidative dehydrogenation process and/or above-mentioned oxidation process can be obtained by means of a process wherein the catalyst precursor is contacted with a gas mixture comprising ammonia and water, which gas mixture further comprises oxygen and/or an inert gas, at an elevated temperature.

Accordingly, the present invention relates to a process for preparing a catalyst for alkane oxidative dehydrogenation and/or alkene oxidation, which catalyst is a mixed metal oxide catalyst containing molybdenum, vanadium, niobium and optionally tellurium, wherein the process comprises:

a) preparing a catalyst precursor containing molybdenum, vanadium, niobium and optionally tellurium;

b) optionally contacting the catalyst precursor obtained in step a) with oxygen and/or an inert gas at an elevated temperature;

c) contacting the catalyst precursor obtained in step a) or step b) with a gas mixture comprising ammonia and water, which gas mixture further comprises oxygen and/or an inert gas, at an elevated temperature; and d) optionally contacting the catalyst precursor obtained in step c) with an inert gas at an elevated temperature.

Further, the present invention relates to a catalyst obtainable by the above-mentioned process.

Further, the present invention relates to a process of the oxidative dehydrogenation of an alkane containing 2 to 6 carbon atoms and/or the oxidation of an alkene containing 2 to 6 carbon atoms, wherein the catalyst obtained or obtainable by the above-mentioned process is used.

DETAILED DESCRIPTION OF THE INVENTION

The process of the present invention comprises steps a), b), c) and d), wherein steps b) and d) are optional, as described hereinbelow. Said process may comprise one or more intermediate steps between steps a) and b), between steps b) and c), and between steps c) and d). Further, said process may comprise one or more additional steps preceding step a) and/or following step d).

While the process of the present invention and gas mixtures or gas streams used in said process are described in terms of "comprising", "containing" or "including" one or more various described steps and components, respectively, they can also "consist essentially of" or "consist of" said one or more various described steps and components, respectively.

In the context of the present invention, in a case where a gas mixture or gas stream or a catalyst comprises two or more components, these components are to be selected in an overall amount not to exceed 100 vol. % or 100 wt. %, respectively.

Further, where upper and lower limits are quoted for a property then a range of values defined by a combination of any of the upper limits with any of the lower limits is also implied.

In step c) of the catalyst preparation process of the present invention, the catalyst precursor obtained in step a) or step b) is contacted with a gas mixture comprising ammonia ($NH_3$) and water ($H_2O$), which gas mixture further comprises oxygen (O2) and/or an inert gas, at an elevated temperature. Surprisingly, it has been found that the presence of ammonia and water in said gas mixture comprising oxygen and/or an inert gas advantageously results in a higher activity of the final catalyst in alkane oxidative dehydrogenation and alkene oxidation.

Preferably, the gas mixture in step c) comprises 0.01 to 10 vol. %, more preferably 0.01 to 5 vol. %, more preferably 0.05 to 2 vol. %, most preferably 0.05 to 1.0 vol. % of ammonia, based on the total volume of the gas mixture.

Further, preferably, the gas mixture in step c) comprises 1 to 50 vol. %, more preferably 1 to 30 vol. %, more preferably 3 to 20 vol. %, most preferably 5 to 18 vol. % of water, based on the total volume of the gas mixture.

Still further, preferably, the gas mixture in step c) comprises 5 to 50 vol. %, more preferably 5 to 40 vol. %, more preferably 5 to 30 vol. %, more preferably 5 to 25 vol. %, more preferably 10 to 21 vol. %, most preferably 15 to 21 vol. % of oxygen, based on the total volume of the gas mixture.

In step c), the gas mixture comprising ammonia and water and further comprising oxygen and/or an inert gas may be provided in a number of ways. The catalyst precursor obtained in step a) or step b) may be contacted with a gas stream comprising oxygen and/or an inert gas to which gas stream ammonia and water are added before the catalyst precursor is contacted with the gas stream. Further, the catalyst precursor obtained in step a) or step b) may be contacted with multiple gas streams comprising one or more of ammonia and water and oxygen and/or an inert gas. Still further, the catalyst precursor obtained in step a) or step b) may be contacted with a gas mixture comprising oxygen and/or an inert gas and subjected to an elevated temperature in step c) thereby releasing ammonia and water, resulting in a gas mixture comprising ammonia and water and oxygen and/or an inert gas. If in the latter case, the gas mixture is a gas stream, the resulting gas stream comprising ammonia and water and oxygen and/or an inert gas is preferably recycled so that it is contacted with the precursor again. Alternatively, in the latter case, (i) a gas mixture comprising oxygen and/or an inert gas and (ii) the catalyst precursor obtained in step a) or step b) may be co-currently fed to a continuously operated calcination unit and contacted therein with each other at said elevated temperature. Further, in the latter cases it is preferred that in step a) the catalyst precursor is prepared using metal salts that may release ammonia upon heating, such as ammonium metal salts as further described below. Still further, in this case the water may be any crystal water in the catalyst precursor that may be released upon heating. Alternatively, the catalyst precursor obtained in step a) or step b) may be treated, for example impregnated, with ammonia and water or with an ammonia and water releasing agent before the catalyst precursor is contacted with a gas stream comprising oxygen and/or an inert gas. Ammonia and water may be provided in the form of an aqueous ammonia solution. Further, said ammonia and water releasing agent may be an aqueous solution of ammonium carbonate. A catalyst precursor that has been treated, for example impregnated, with such ammonium carbonate solution will generate ammonia and water upon heating at an elevated temperature.

In addition to ammonia and water, the gas mixture in step c) comprises oxygen and/or an inert gas. Said inert gas may be selected from the group consisting of the noble gases, nitrogen ($N_2$) and carbon dioxide ($CO_2$), preferably from the group consisting of the noble gases and nitrogen ($N_2$). More preferably, the inert gas is nitrogen or argon, most preferably nitrogen.

Optionally, the inert gas in step c) may comprise oxygen in an amount of less than 10,000 parts per million by volume (ppmv), based on the total volume of the gas mixture comprising the inert gas and oxygen. The amount of oxygen may be of from 10 to less than 10,000 ppmv. Preferably, the amount of oxygen is of from 100 to 9,500, more preferably 400 to 9,000, more preferably 600 to 8,500, more preferably 800 to 8,000, most preferably 900 to 7,500 parts per million by volume.

In step c), any source containing oxygen, such as for example air, may be used. The gas mixture in step c) may comprise ammonia and water in the above-described amounts and for the remainder air.

The temperature in step c) may vary within wide ranges and may be of from 120 to 900° C. or 150 to 700° C. Preferably, in step c) the temperature is of from 120 to 500° C., more preferably 120 to 400° C., more preferably 150 to 375° C., most preferably 150 to 350° C. In case the gas mixture in step c) consists of an inert gas, which inert gas may contain a small amount of oxygen as described above, and ammonia and water, the temperature in step c) may be higher, for example in the range of from 400 to 800° C. or 500 to 700° C.

In the catalyst preparation process of the present invention, step c) may be preceded by optional step b) comprising contacting the catalyst precursor obtained in step a) with oxygen and/or an inert gas at an elevated temperature. It is preferred that in optional step b) no ammonia and water are added.

Said inert gas in optional step b) may be selected from the group consisting of the noble gases, nitrogen ($N_2$) and carbon dioxide ($CO_2$), preferably from the group consisting of the noble gases and nitrogen ($N_2$). More preferably, the inert gas is nitrogen or argon, most preferably nitrogen.

Optionally, the inert gas in optional step b) may comprise oxygen in an amount of less than 10,000 parts per million by volume (ppmv), based on the total volume of the gas mixture comprising the inert gas and oxygen. The amount of oxygen may be of from 10 to less than 10,000 ppmv. Preferably, the amount of oxygen is of from 100 to 9,500, more preferably 400 to 9,000, more preferably 600 to 8,500, more preferably 800 to 8,000, most preferably 900 to 7,500 parts per million by volume.

In optional step b), any source containing oxygen, such as for example air, may be used.

In optional step b), the catalyst precursor obtained in step a) may be contacted with a gas consisting of air or with a gas consisting of one or more inert gases.

Preferably, in optional step b) the temperature is of from 120 to 500° C., more preferably 120 to 400° C., more preferably 150 to 375° C., most preferably 150 to 350° C. The temperatures in steps b) and c) may be the same.

Further, in optional step d) of the catalyst preparation process of the present invention, the catalyst precursor obtained in step c) is contacted with an inert gas at an elevated temperature. It is preferred that in optional step d) no ammonia and water are added. In optional step d), any ammonia and water originating from step c) may be present, for example in an amount of at most 0.1 wt. % of ammonia and 1 wt. % of water, based on the total weight of the catalyst precursor.

Said inert gas in optional step d) may be selected from the group consisting of the noble gases, nitrogen ($N_2$) and carbon dioxide ($CO_2$), preferably from the group consisting of the noble gases and nitrogen ($N_2$). More preferably, the inert gas is nitrogen or argon, most preferably nitrogen.

Optionally, the inert gas in optional step d) may comprise oxygen in an amount of less than 10,000 parts per million by volume (ppmv), based on the total volume of the gas mixture comprising the inert gas and oxygen. The amount of oxygen may be of from 10 to less than 10,000 ppmv. Preferably, the amount of oxygen is of from 100 to 9,500, more preferably 400 to 9,000, more preferably 600 to 8,500, more preferably 800 to 8,000, most preferably 900 to 7,500 parts per million by volume.

In optional step d), the catalyst precursor obtained in step c) may be contacted with a gas consisting of one or more inert gases.

Further, preferably, in optional step d) the temperature is of from 300 to 900° C., preferably 400 to 800° C., more preferably 500 to 700° C. It is preferred that the temperature in optional step d) is at least 300° C., more preferably at least 400° C., more preferably at least higher than 420° C., more preferably at least 430° C., more preferably at least 450° C., more preferably at least higher than 450° C., most preferably at least 500° C. The catalyst treatments in steps b), c) and d) of the catalyst preparation process of the present invention may also be referred to as catalyst calcinations.

Preferably, above-described step d) is part of the catalyst preparation process of the present invention. In case the latter process comprises both step c) and step d), there is preferably no intermediate treatment step between said steps c) and d). Cooling may be carried out between said steps c) and d). Step a) of the catalyst preparation process of the present invention comprises preparing a catalyst precursor containing molybdenum, vanadium, niobium and optionally tellurium. Within the present specification, the "catalyst precursor" is a metal-containing substance, containing molybdenum, vanadium, niobium and optionally tellurium, that still needs to be converted to form the metal oxide. The catalyst precursor obtained in step a) is a solid. Any known way to prepare such catalyst precursor may be applied. For example, the catalyst precursor may be prepared by a hydrothermal process using a solution or slurry, preferably an aqueous solution or slurry, comprising molybdenum, vanadium, niobium and optionally tellurium or multiple solutions or slurries, preferably aqueous solutions or slurries, comprising one or more of said metals. Alternatively, the catalyst precursor may be prepared by precipitation of one or more solutions, preferably aqueous solutions, comprising molybdenum, vanadium, niobium and optionally tellurium.

The latter precipitation process may comprise:

preparing two solutions, preferably aqueous solutions, one solution comprising molybdenum, vanadium and optionally tellurium, which solution is preferably prepared at slightly elevated temperature, for example 50 to 90° C., preferably 60 to 80° C., and another solution comprising niobium, which solution is preferably prepared at about, or slightly above, room temperature, for example 15 to 40° C., preferably 20 to 35° C.;

combining said two solutions resulting in a precipitate comprising molybdenum, vanadium, niobium and optionally tellurium, which said precipitate may have the appearance of a gel, slurry or dispersion;

recovering the precipitate thus obtained (the catalyst precursor); and optionally drying the precipitate.

The precipitate thus obtained may be recovered by removing the solvent, preferably water, which can be done by drying, filtration or any other known means for recovery, preferably by drying, for example by evaporation to dryness, for example with the aid of a rotating evaporator, for example at a temperature of from 30 to 70° C., preferably 40 to 60° C., or for example by drying in an oven at a temperature of from 60 to 140° C., or for example by spray drying. The recovered solid may be dried or further dried at a temperature in the range of from 60 to 150° C., suitably 80 to 130° C., more suitably 80 to 120° C.

In step a) of the above-mentioned catalyst preparation process, solutions comprising molybdenum, vanadium, niobium and/or optionally tellurium, preferably aqueous solutions, may first be prepared by admixing. The elements Mo, V, Nb and optionally Te can be incorporated into the admixing step as pure metallic elements, as salts, as oxides, as hydroxides, as alkoxides, as acids, or as mixtures of two or more of the above-mentioned forms. As salts, sulfates, nitrates, oxalates, halides, or oxyhalides may be used. For example, the Mo can be incorporated as molybdic acid, ammonium heptamolybdate, molybdenum chlorides, molybdenum acetate, molybdenum ethoxide and/or molybdenum oxides, preferably ammonium heptamolybdate. The V can be incorporated as ammonium vanadate, ammonium metavanadate, vanadium oxide, vanadyl sulfate, vanadyl oxalate, vanadium chloride or vanadyl trichloride, preferably ammonium metavanadate. The Nb can be incorporated as niobium pentoxide, niobium oxalate, ammonium niobate oxalate, niobium chloride or Nb metal, preferably ammonium niobate oxalate. The optional Te can be incorporated as telluric acid, tellurium dioxide, tellurium ethoxide, tellurium chloride and metallic tellurium, preferably telluric acid.

In the present invention, the catalyst is a mixed metal oxide catalyst containing molybdenum, vanadium, niobium and optionally tellurium as the metals, which catalyst may have the following formula:

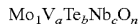

$$Mo_1V_aTe_bNb_cO_n$$

wherein:

a, b, c and n represent the ratio of the molar amount of the element in question to the molar amount of molybdenum (Mo);

a (for V) is from 0.01 to 1, preferably 0.05 to 0.60, more preferably 0.10 to 0.40, more preferably 0.20 to 0.35, most preferably 0.25 to 0.30;

b (for Te) is either 0 or from >0 to 1, preferably 0.01 to 0.40, more preferably 0.05 to 0.30, more preferably 0.05 to 0.20, most preferably 0.09 to 0.15;

c (for Nb) is from >0 to 1, preferably 0.01 to 0.40, more preferably 0.05 to 0.30, more preferably 0.10 to 0.25, most preferably 0.14 to 0.20; and n (for O) is a number which is determined by the valency and frequency of elements other than oxygen.

Further, the present invention relates to a process of the oxidative dehydrogenation of an alkane containing 2 to 6 carbon atoms and/or the oxidation of an alkene containing 2 to 6 carbon atoms, wherein the catalyst obtained or obtainable by the above-mentioned catalyst preparation process is used.

Preferably, in said alkane oxidative dehydrogenation process, the alkane containing 2 to 6 carbon atoms is a linear alkane in which case said alkane may be selected from the group consisting of ethane, propane, butane, pentane and hexane. Further, preferably, said alkane contains 2 to 4 carbon atoms and is selected from the group consisting of ethane, propane and butane. More preferably, said alkane is ethane or propane. Most preferably, said alkane is ethane.

Further, preferably, in said alkene oxidation process, the alkene containing 2 to 6 carbon atoms is a linear alkene in which case said alkene may be selected from the group consisting of ethylene, propylene, butene, pentene and hexene. Further, preferably, said alkene contains 2 to 4 carbon atoms and is selected from the group consisting of ethylene, propylene and butene. More preferably, said alkene is ethylene or propylene.

The product of said alkane oxidative dehydrogenation process may comprise the dehydrogenated equivalent of the alkane, that is to say the corresponding alkene. For example, in the case of ethane such product may comprise ethylene, in the case of propane such product may comprise propylene, and so on. Such dehydrogenated equivalent of the alkane is initially formed in said alkane oxidative dehydrogenation process. However, in said same process, said dehydrogenated equivalent may be further oxidized under the same conditions into the corresponding carboxylic acid which may or may not contain one or more unsaturated double carbon-carbon bonds. As mentioned above, it is preferred that the alkane containing 2 to 6 carbon atoms is ethane or propane. In the case of ethane, the product of said alkane oxidative dehydrogenation process may comprise ethylene and/or acetic acid, preferably ethylene. Further, in the case of propane, the product of said alkane oxidative dehydrogenation process may comprise propylene and/or acrylic acid, preferably acrylic acid.

The product of said alkene oxidation process comprises the oxidized equivalent of the alkene. Preferably, said oxidized equivalent of the alkene is the corresponding carboxylic acid. Said carboxylic acid may or may not contain one or more unsaturated double carbon-carbon bonds. As mentioned above, it is preferred that the alkene containing 2 to 6 carbon atoms is ethylene or propylene. In the case of ethylene, the product of said alkene oxidation process may comprise acetic acid. Further, in the case of propylene, the product of said alkene oxidation process may comprise acrylic acid.

The present alkane oxidative dehydrogenation process and/or alkene oxidation process may comprise subjecting a stream comprising the alkane containing 2 to 6 carbon atoms or a stream comprising the alkene containing 2 to 6 carbon atoms or a stream comprising both said alkane and said alkene to oxydehydrogenation conditions. Said stream may be contacted with an oxidizing agent, thereby resulting in oxidative dehydrogenation of the alkane and/or oxidation of the alkene. The oxidizing agent may be any source containing oxygen, such as for example air.

Ranges for the molar ratio of oxygen to the alkane and/or alkene which are suitable, are of from 0.01 to 1, more suitably 0.05 to 0.5.

Preferably, the catalyst of the present invention is used as a pelletized catalyst, for example in the form of a fixed catalyst bed, or a powdered catalyst, for example in the form of a fluidized catalyst bed.

Examples of oxydehydrogenation processes, including catalysts and other process conditions, are for example disclosed in above-mentioned U.S. Pat. No. 7,091,377, WO2003064035, US20040147393, WO2010096909 and US20100256432, the disclosures of which are herein incorporated by reference.

The amount of the catalyst in said process is not essential. Preferably, a catalytically effective amount of the catalyst is used, that is to say an amount sufficient to promote the alkane oxydehydrogenation and/or alkene oxidation reaction. Although a specific quantity of catalyst is not critical to the invention, preference may be expressed for use of the catalyst in such an amount that the gas hourly space velocity (GHSV) is of from 100 to 50,000 hr$^{-1}$, suitably of from 200 to 20,000 hr$^{-1}$, more suitably of from 300 to 15,000 hr$^{-1}$, most suitably of from 500 to 10,000 hr$^{-1}$.

In the alkane oxidative dehydrogenation process and/or alkene oxidation process of the present invention, typical reaction pressures are 0.1-20 bara, and typical reaction temperatures are 100-600° C., suitably 200-500° C.

In general, the product stream comprises water in addition to the desired product. Water may easily be separated from said product stream, for example by cooling down the product stream from the reaction temperature to a lower temperature, for example room temperature, so that the water condenses and can then be separated from the product stream.

The invention is further illustrated by the following Examples.

EXAMPLES

A) Preparation of the Catalysts

A number of mixed metal oxide catalysts containing molybdenum (Mo), vanadium (V), niobium (Nb) and tellurium (Te) was prepared, for which catalysts the molar ratio of said 4 metals was $Mo_1V_{0.29}Nb_{0.17}Te_{0.12}$, in the following way.

Two solutions were prepared. Solution 1 was obtained by dissolving 15.8 parts by weight (pbw) of ammonium niobate oxalate and 4 pbw of oxalic acid dihydrate in 160 pbw of water at room temperature. Solution 2 was prepared by dissolving 35.6 pbw of ammonium heptamolybdate tetrahydrate, 6.9 pbw of ammonium metavanadate and 5.8 pbw of telluric acid ($Te(OH)_6$) in 200 pbw of water at 70° C. 7 pbw of concentrated nitric acid was then added to solution 2.

The 2 solutions were combined, by quickly pouring solution 2 into solution 1 under vigorous stirring, which yielded an orange gel-like precipitate (suspension) having a temperature of about 45° C. This suspension was then aged for about 15 minutes. The suspension was then dried by means of spray drying to remove the water, which yielded a dry, fine powder (the catalyst precursor). Said spray drying was carried out by using an air temperature of 180° C. resulting in a solid temperature of 80° C.

For some catalysts, as indicated in the table below, the spray-dried catalyst precursor was first pre-calcined in static air at 200° C. for 2 hours, after which it was cooled down to room temperature.

Subsequently, a calcination was carried out in a tube oven wherein the catalyst precursor was contacted with a gas stream comprising air or nitrogen ($N_2$) and varying amounts of ammonia ($NH_3$) and water ($H_2O$). In the air experiments, the gas mixture in said stream comprised oxygen, nitrogen, ammonia and water. In the nitrogen experiments, the gas mixture in said stream comprised nitrogen, ammonia and water, but no oxygen. The $NH_3$ and $H_2O$ contents are indicated in the table below, as well as the use of either an air stream or a nitrogen stream. In preparing all catalysts except Catalysts D2, D3 and D4, the catalyst precursor was heated from room temperature to 320° C. at a rate of 100° C./hour and kept at 320° C. for 2 hours. In preparing Catalysts D2, D3 and D4, the catalyst precursor was heated from room temperature to 600° C. at a rate of 100° C./hour and kept at 600° C. for 2 hours. $NH_3$ and $H_2O$ were only fed into the above-mentioned air stream or nitrogen stream when a certain temperature was reached, as indicated in the table below. Thus, before $NH_3$ and $H_2O$ were fed, said stream only comprised air or nitrogen. The flow of the stream in this calcination step was 15 Nl/hr. The catalyst precursor was then cooled down to room temperature.

The cooled catalyst precursor was then removed from the tube oven and further calcined in a nitrogen ($N_2$) stream. The catalyst precursor was heated from room temperature to 600° C. at a rate of 100° C./hour and kept at 600° C. for 2 hours, after which the catalyst was cooled down to room temperature. The flow of the stream in this calcination step was 15 Nl/hr.

B) Testing of the Catalysts in Ethane Oxidative Dehydrogenation (ODH)

The catalysts thus prepared were tested for catalytic performance in ethane oxidative dehydrogenation (ODH) in one of 2 different test methods, hereinafter indicated as test methods 1 and 2 (see also the table below).

Test Method 1:

700 mg of a sieve fraction of the catalyst (30-80 mesh) was loaded in a steel reactor having an internal diameter (ID) of 4 mm. A gas stream comprising 55 vol. % of nitrogen, 32 vol. % of ethane and 13 vol. % of oxygen was passed downflow over the catalyst at a flow rate of 26 Nml/minute, at atmospheric pressure and at a temperature of 360° C.

Test Method 2:

100 mg of a sieve fraction of the catalyst (30-80 mesh) was loaded in a quartz reactor having an internal diameter (ID) of 2 mm. A gas stream comprising 39 vol. % of nitrogen, 17 vol. % of helium, 33 vol. % of ethane and 10 vol. % of oxygen was passed downflow over the catalyst at a flow rate of 12 Nml/minute, at a pressure of 3.3 bara and at a temperature of 360° C.

In both said test methods, the conversion of ethane and the product composition were measured with a gas chromatograph (GC) equipped with a thermal conductivity detector (TCD). The table below shows the performance of all of the differently calcined catalysts after about 60 hours on stream.

For example, Catalysts C2 to C5 which were made with feeding varying amounts of water and ammonia in said calcination step, had ethane conversions (ranging from 6% to 34%) which were advantageously higher than that of (reference) Catalyst C1 (0.5%) which was prepared without feeding water and ammonia.

Further, it was found that when the feed of water and ammonia is started at a later stage in the above-described calcination step, similar ethane conversions are obtained as in the case wherein the feed of water and ammonia is started at an earlier stage in said calcination step. In preparing Catalysts A5 and A6, water and ammonia were only fed when a temperature of 280° C. and 320° C., respectively, was reached, resulting in an ethane conversion of 32%. In preparing Catalyst A1, water and ammonia were already fed when a temperature of 160° C. was reached, resulting in a similar ethane conversion, namely 35%.

Catalysts A2, A3 and A4 were prepared in the same way as Catalyst A1, except for the water and ammonia contents. The ethane conversions for Catalysts A2, A3 and A4 were also advantageously high, for example in comparison with the ethane conversion of 0.5% for (reference) Catalyst C1 which was prepared without feeding water and ammonia in said calcination step.

Further, it was found that oxygen (e.g. provided via air) does not have to be fed when feeding water and ammonia in

| Catalyst | Pre-calcined? | Air (1) | N$_2$ (1) | H$_2$O (2) | NH$_3$ (2) | Start H$_2$O/NH$_3$ feed (3) | Stop H$_2$O/NH$_3$ feed (3) | Ethane conversion | Test method |
|---|---|---|---|---|---|---|---|---|---|
| E1* | No  | + | − | 0  | 0   | N/A     | N/A         | 0.2% | 2 |
| E2  | No  | + | − | 13 | 0.5 | 160° C. | end of step | 32%  | 2 |
| C1* | Yes | + | − | 0  | 0   | N/A     | N/A         | 0.5% | 2 |
| C2  | Yes | + | − | 13 | 0.5 | 160° C. | end of step | 34%  | 2 |
| C5  | Yes | + | − | 13 | 2.0 | 160° C. | end of step | 32%  | 2 |
| C3  | Yes | + | − | 13 | 0.1 | 160° C. | end of step | 17%  | 2 |
| C4  | Yes | + | − | 5  | 0.1 | 160° C. | end of step | 6%   | 2 |
| D1  | Yes | − | + | 13 | 0.5 | 160° C. | end of step | 33%  | 2 |
| D2* | Yes | − | + | 0  | 0   | N/A     | N/A         | 0.1% | 1 |
| D3  | Yes | − | + | 13 | 0.5 | 120° C. | end of step | 18%  | 1 |
| D4  | No  | − | + | 13 | 0.5 | 160° C. | 600° C.     | 13%  | 2 |
| A1  | Yes | + | − | 13 | 0.5 | 160° C. | end of step | 35%  | 1 |
| A5  | Yes | + | − | 13 | 0.5 | 280° C. | end of step | 32%  | 1 |
| A6  | Yes | + | − | 13 | 0.5 | 320° C. | end of step | 32%  | 1 |
| A2  | Yes | + | − | 13 | 0.1 | 160° C. | end of step | 23%  | 1 |
| A3  | Yes | + | − | 5  | 0.5 | 160° C. | end of step | 21%  | 1 |
| A4  | Yes | + | − | 5  | 0.1 | 160° C. | end of step | 15%  | 1 |

Explanation table:
(1) H$_2$O and NH$_3$ were fed to either an air stream (+under "Air") or a nitrogen stream (+under "N$_2$").
(2) H$_2$O and NH$_3$ contents are expressed in vol. % on the basis of the total volume of the gas stream. The amount of air or nitrogen was 100 vol. % minus the water and ammonia contents.
(3) The H$_2$O/NH$_3$ feed was started at the time the indicated temperature was reached. Further, the H$_2$O/NH$_3$ feed was stopped either at the end of this calcination step or, earlier, at the time the indicated temperature was reached.
N/A = not applicable
*= Reference catalyst (not in accordance with the invention)

Surprisingly, it was found that the presence of water and ammonia in the gas stream used in the above-described calcination step advantageously results in a higher activity of the final catalyst in alkane oxidative dehydrogenation. This is demonstrated by the data in the table above.

For example, Catalyst E2 which was made with feeding water and ammonia in said calcination step, had an ethane conversion (32%) which was advantageously higher than that of (reference) Catalyst E1 (0.2%), which was prepared without feeding water and ammonia in said calcination step. Both said Catalysts E1 and E2 were prepared without pre-calcination.

For other catalysts which were prepared with pre-calcination, a positive effect on ethane conversion by feeding water and ammonia in the above-described calcination step is also shown in the table above.

the above-described calcination step. An inert gas may be fed instead. For example, in preparing Catalyst D1, nitrogen (N$_2$) was used instead of air in the above-described calcination step. The ethane conversion for Catalyst D1 was similar, namely 33%, to the ethane conversion for Catalyst C2 wherein air was used in said calcination step, which was 34%.

Further, in preparing Catalysts D3 and D4, nitrogen (N$_2$) was used instead of air in the above-described calcination step and the temperature during said step was further increased to 600° C., resulting in ethane conversions of 18% and 13%, respectively, which is advantageously higher than the ethane conversion of 0.1% for (reference) Catalyst D2, which was prepared in the same way as Catalyst D3, with the proviso that in preparing (reference) Catalyst D2 no water and ammonia were fed.

That which is claimed is:

1. A process for preparing a catalyst for alkane oxidative dehydrogenation and/or alkene oxidation, which catalyst is a mixed metal oxide catalyst containing molybdenum, vanadium, niobium and optionally tellurium, wherein the process comprises:
   a) preparing a catalyst precursor containing molybdenum, vanadium, niobium and optionally tellurium;
   b) optionally contacting the catalyst precursor obtained in step a) with oxygen and/or an inert gas at an elevated temperature;
   c) contacting the catalyst precursor obtained in step a) or step b) with a gas mixture comprising ammonia and water, which gas mixture further comprises oxygen and/or an inert gas, at an elevated temperature which is of from 120 to 900° C.; and
   d) contacting the catalyst precursor obtained in step c) with an inert gas at an elevated temperature which is at least higher than 420° C.

2. The process according to claim 1, wherein in step b) the temperature is of from 120 to 500° C.

3. The process according to claim 1, wherein in step c) the temperature is of from 150 to 700° C.

4. The process according to claim 1, wherein in step d) the temperature is of from higher than 420 to 900° C.

5. The process according to claim 1, wherein the gas mixture in step c) comprises 0.01 to 10 vol. % of ammonia, based on the total volume of the gas mixture.

6. The process according to claim 1, wherein the gas mixture in step c) comprises 1 to 50 vol. % of water, based on the total volume of the gas mixture.

7. A catalyst obtained by the process according to claim 1.

8. A process of the oxidative dehydrogenation of an alkane containing 2 to 6 carbon atoms and/or the oxidation of an alkene containing 2 to 6 carbon atoms, said process comprising, contacting the catalyst obtained by the process according to claim 1, with the alkane and/or the alkene.

9. The process according to claim 8, wherein the alkane is ethane or propane and the alkene is ethylene or propylene.

* * * * *